(12) United States Patent
Oshima et al.

(10) Patent No.: US 7,333,186 B2
(45) Date of Patent: Feb. 19, 2008

(54) METHOD AND DEVICE FOR MEASURING BIOLOGICAL INFORMATION

(75) Inventors: Kiyoko Oshima, Shijonawate (JP); Shinji Uchida, Neyagawa (JP); Masahiko Shioi, Katano (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 340 days.

(21) Appl. No.: 11/081,088

(22) Filed: Mar. 16, 2005

(65) Prior Publication Data
US 2005/0209514 A1 Sep. 22, 2005

(30) Foreign Application Priority Data
Mar. 17, 2004 (JP) ............... 2004-076810

(51) Int. Cl.
*G01N 33/48* (2006.01)
*A61B 5/00* (2006.01)

(52) U.S. Cl. .................. 356/39; 600/310; 600/316
(58) Field of Classification Search ............ None
See application file for complete search history.

(56) References Cited

U.S. PATENT DOCUMENTS

| | | | |
|---|---|---|---|
| 5,068,536 A | 11/1991 | Rosenthal | |
| 5,077,476 A | 12/1991 | Rosenthal | |
| 5,086,229 A | 2/1992 | Rosenthal et al. | |
| 5,204,532 A | 4/1993 | Rosenthal | |
| 5,218,207 A * | 6/1993 | Rosenthal | 250/341.1 |
| 5,237,178 A * | 8/1993 | Rosenthal et al. | 250/341.7 |
| 5,362,966 A | 11/1994 | Rosenthal et al. | |
| 5,365,066 A | 11/1994 | Krueger, Jr. et al. | |
| 5,370,114 A | 12/1994 | Wong et al. | |
| 5,436,455 A | 7/1995 | Rosenthal et al. | |
| 5,438,201 A | 8/1995 | Rosenthal et al. | |
| 5,574,283 A | 11/1996 | Quintana | |
| 5,676,143 A * | 10/1997 | Simonsen et al. | 600/316 |
| 5,782,757 A * | 7/1998 | Diab et al. | 600/323 |
| 5,924,982 A * | 7/1999 | Chin | 600/310 |
| 6,066,847 A | 5/2000 | Rosenthal | |
| 6,213,952 B1 * | 4/2001 | Finarov et al. | 600/491 |
| 6,424,851 B1 * | 7/2002 | Berman et al. | 600/322 |

FOREIGN PATENT DOCUMENTS

| | | |
|---|---|---|
| JP | 05-508336 | 11/1993 |
| JP | 09-113439 | 5/1997 |
| WO | WO92/00513 | 1/1992 |
| WO | WO 01/79818 A2 | 10/2001 |

* cited by examiner

*Primary Examiner*—Layla G. Lauchman
*Assistant Examiner*—Jonathan Skovholt
(74) *Attorney, Agent, or Firm*—McDermott Will & Emery LLP

(57) ABSTRACT

In order to precisely determine a stable measuring region appropriate for a measurement of biological information, and to measure a concentration of a specific component, i.e. biological information, without inconsistency, a biological information measuring device is provided with, a measuring region determining means for determining a measuring region in between an eponychium and a distal interphalangeal joint; an information detector for applying a light to measuring region; a light source for entering a light to information detector; a light detector for detecting a light which exits from the information detector; and a processor for measuring specific component based on information obtained from light detector.

9 Claims, 6 Drawing Sheets

(a)

(b)

(c)

(a)

(b)

METHOD AND DEVICE FOR MEASURING BIOLOGICAL INFORMATION

BACKGROUND OF THE INVENTION

The present invention relates to method and device for measuring biological information in which a specific component having biological information such as glucose, cholesterol, urea, or neutral fat is measured noninvasively by making use of transmitted light, reflected light, scattered light, or transmitted/reflected light.

Recently, a device for measuring glucose of a human subject noninvasively has been proposed.

For example, as described in Yamamura et al., Comprehensive Handbook of Clinical Dermatology 3B: Structure and Function of Skin II, Nakayama Shoten, 1982, it is known that a concentration of glucose in epidermis of a living body changes in direct proportion to a change in a blood-sugar level. Also, as described in Japanese Unexamined Patent Publication No. Hei 5-508336, for example, the method is known in which a near infrared ray of 600 nm-1100 nm is applied to a human subject and a blood-sugar level is obtained by analyzing a light component having a specific wavelength that passed through the human subject.

Further, there has been known the method using a mid infrared ray and an ATR (attenuated total reflectance) prism in which attenuated total reflection of incident light is repeated at an interface between a reflection surface of the ATR prism and a living body, and then light emitted to the outside of the ATR prism is analyzed. For example, in Japanese Laid-Open Patent Publication No. Hei 9-113439, a measuring method by sandwiching an ATR prism in a mouth or between fingers is proposed.

In this method of Japanese Laid-Open Patent Publication No. Hei 9-113439, an evanescent wave (so-called penetrating wave) is applied to a quantitative analysis. A light traveling in an ATR prism slightly seep out into lips or fingers and then is reflected. Therefore, the light is affected by components in a body fluid existing in the lips or fingers. For this reason, variations in reflectance, absorptance, and the like of the body fluid can be detected by measuring the amount of the reflected light, and therefore, information about the components in the body fluid can be obtained.

According to Japanese Unexamined Patent Publication No. Hei 5-508336 and Japanese Laid-Open Patent Publication No. Hei 9-113439 above, since a component such as glucose in a living body has a light absorption peak, when a light of a wave number corresponding to this absorption peak is applied to a living body, the amount of the light absorbed differs corresponding to a glucose concentration in the living body. Therefore, by measuring a returned light from the living body, information regarding a glucose concentration can be obtained. Here, the information regarding a concentration refers to an absolute value of the concentration, variations of the concentration over time, and the like.

Although the evanescent wave is not used, Japanese Laid-Open Patent Publication No. Hei 3-173535 discloses a method in which a glucose concentration in a living body is obtained by applying a near infrared light from a light source to a living body, and energy of a light passed through the living body is measured. To be more specific, a method is proposed in which biological information is measured by passing a light to a finger, specifically to a nail part of the finger.

BRIEF SUMMARY OF THE INVENTION

However, the above conventional optical measurements have the following problems.

The method described in Japanese Unexamined Patent Publication No. Hei 5-508336, and Japanese Laid-Open Patent Publication No. Hei 3-173535 use a near infrared light. On one hand, a near infrared light easily passes through an aqueous solution or a living body and is appropriate for analysis, due to its small absorption intensity against water compared with an infrared light. On the other hand, when a near infrared light is used, since absorption peaks of various components overlap complicatedly, it is difficult to obtain information on an individual component compared with the case when an infrared light is used.

A skin of a living body is composed of epidermis, dermis, subcutaneous tissue, and the like. In dermis, blood vessels exist and circulate the blood. Dermis includes many constructs such as sweat glands, hair roots, arrector pili muscles, and the like. Epidermis has a four-layered structure including a horny layer, a granular layer, a prickle layer, and a basal layer, from the outermost. The horny layer is so-called "dead cell" and no metabolic activity occurs in here.

Therefore, when a near infrared light is applied to a skin, as described in Japanese Unexamined Patent Publication No. Hei 5-508336, the light reaches till dermis and red blood cells, which are the light scattering body in blood, move during the measurement to change scattering state of the light, thereby affecting signals to be obtained. Constructs such as sweat glands, hair roots, arrector pili muscles, and the like also affect the signals.

Additionally, when a measurement is conducted by passing through a light at a part of a nail, as in Japanese Laid-Open Patent Publication No. Hei 3-173535, it is difficult to measure biological information accurately; because, little glucose is included in a nail part, a nail prevents a transmission of a light, and a light scatters in a nail.

Also, an evanescent wave used in the conventional method in Japanese Laid-Open Patent Publication No. Hei 9-113439 using attenuated total reflectance only penetrates the measurement subject to the depth of the order of the wavelength and the measurement can be conducted only to a shallow surface depth.

However, a nail part and a horny layer which is the outermost surface of skin include few components which give biological information, and affect as an obstructive part in an optical measurement. The horny layer has a different thickness depending on regions, and the amount of light reaching an inner part of the skin varies according to the thickness of the horny layer, thereby making the measurement results inconsistent and unstable, due to the changes in the detected signal.

Also, in the case the measurement is conducted using an evanescent wave at lip mucous membrane which does not have a horny layer, when saliva is interposed, there is a possibility that a thickness of saliva changes during the measurement or every time the measurement is conducted. The variations in a thickness of the saliva layer change the amount of light reaching an inner part of the skin, and signals to be detected will change, making the measurement results inconsistent and unstable, due to the changes in the detected signal.

An object of the present invention is to solve the above problems in the past, and more specifically, the object of the present invention is to provide a method and a device for measuring biological information, in which a stable measuring region appropriate for a measurement of biological information is precisely determined, and a concentration of a specific component as biological information can be measured at a stable measuring region appropriate for a measurement of biological information.

In order to solve the above problems, the present invention provides a biological information measuring device for measuring a concentration of a specific component included in a living body, comprising:

a measuring region determining means for determining a measuring region in between an eponychium and a distal interphalangeal joint, an information detector for applying a light to the measuring region and detecting a light which exits from the measuring region, a light source for entering a light to the information detector contacting said measuring region, a light detector for detecting a light which exits from the information detector contacting the measuring region, and a processor for measuring the specific component based on information obtained from the light detector.

It is preferable that the device for measuring biological information has an abutting means for abutting the information detector to the measuring portion.

It is also preferable that the measuring region determining means determines the measuring region based on a difference between signal information of light applied to a nail and signal information of light applied to a skin.

Further, it is preferable that the measuring region determining means has a visual identification means capable of identifying a certain position. As to the visual identification means, a combination of a transparent window, and a reference line which is provided in the reference window for positioning a measuring region can be used.

Furthermore, the measuring region determining means may detect an elevation change which exists due to inherent skin structure.

Furthermore, the present invention provides a biological information measuring method for measuring a concentration of a specific component included in a living body, comprising the steps of:

(1) determining a measuring region in between an eponychium and a distal interphalangeal joint;

(2) detecting a light which exits from the measuring region, after an entrance into the measuring region; and (3) specifying a concentration of a specific component of the measuring region based on the light detected in the step (2).

It is preferable that in the step (1), said measuring region is determined based on a difference between signal information of light applied to a nail and signal information of light applied to a skin.

Further, in the step (1), the measuring region may be determined visually.

Furthermore, in the step (1), the measuring region may be determined by detecting an elevation change which exists due to inherent skin structure.

According to method and device for measuring biological information of present invention, since a measuring region is precisely determined in between an eponychium and a distal interphalangeal joint, as in the above, a concentration of a specific component as biological information can be measured without inconsistency at a stable measuring region appropriate for measuring biological information.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Hereinafter, preferred embodiments to carry out the present invention will be described with reference to the drawings. In the following description, same reference numbers are used for the same or corresponding part, and repetitive description may be omitted.

Figure 1:
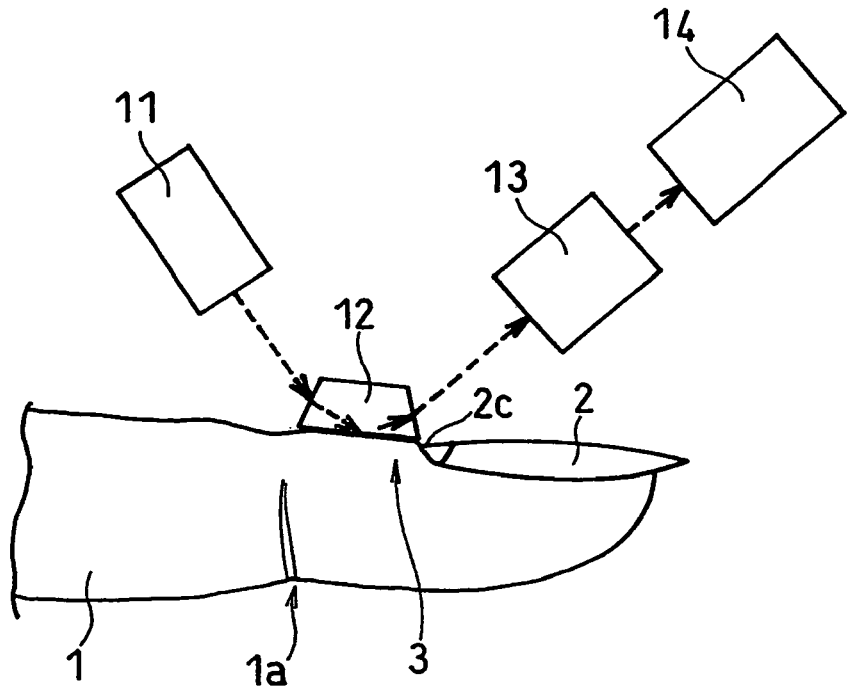
FIG. 1 is a view illustrating a method for measuring biological information according to the present invention.

First, a method of measuring biological information according to the present invention will be described in detail with reference to the drawings. However, the present invention is not limited thereto. FIG. 1 is a view illustrating a method for measuring biological information according to the Embodiment 1 of the present invention.

In step (1), as shown in FIG. 1, a measuring region in between an eponychium 2c and a distal interphalangeal joint 1a is determined, and then the information detector 12 is brought into contact with the measuring region.

Then, in step (2), the light is entered from the light source 11 to the information detector 12, and an incident light was absorbed and reflected to travel through the information detector 12. At this time, an amount of light corresponding to an amount of a specific component included in the measuring region is absorbed, and then a light exits from the information detector 12. Then, the light exits from the information detector 12 is detected by the light detector 13.

Next, in the step (3), the information obtained from the detected light in the step (2) is processed and calculated by a signal processor 14 to specify a concentration of the specific component in the measuring region.

The light detector 13 used in the step (2), and the signal processor 14 used in the step (3) are described in detail later.

Figure 2:
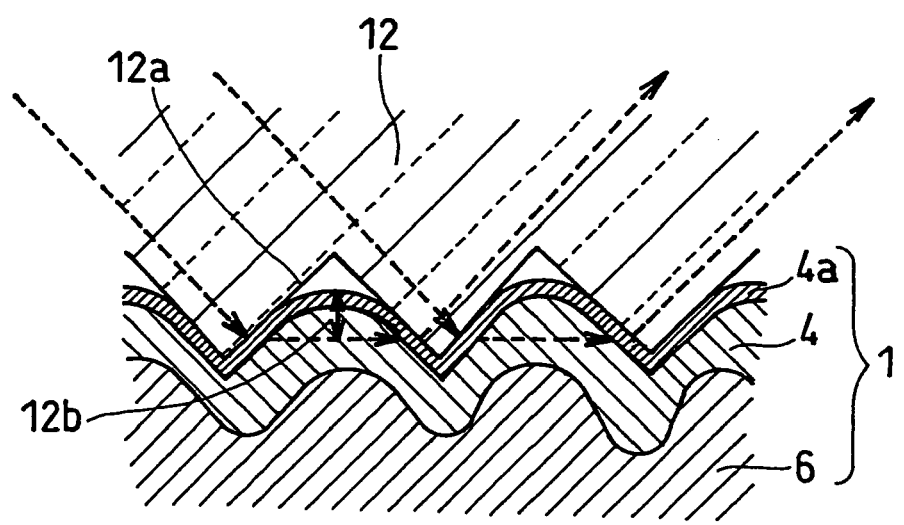
FIG. 2 is an enlarged sectional view illustrating an information detector and a measuring region making contact with each other according to a method for measuring biological information of the present invention.

Here, a schematically enlarged sectional view illustrating a part between a sensing surface of the information detector 12 and the measuring region is shown in FIG. 2. As shown in FIG. 2, the sensing surface 12a of the information detector 12 is formed to have V-shapes, and is in close contact with, while pressing, a skin surface of the measuring region of the finger. In this measuring region, a horny layer 4a is followed by an epidermis 4 and a dermis 6, from the outermost skin surface.

In the information detector 12, the sensing surface 12a is structured to have a form of V-shapes so that the light passes through the epidermis 4 including the horny layer 4 and the dermis 6.

As mentioned above, the epidermis 4 includes the horny layer 4a, the granular layer, the prickle layer, and the basal layer. However, in this specification and figures, detailed structures of the layers other than the horny layer 4a are omitted.

The cells forming the epidermis 4 other than the cells of the horny layer 4a are living cells. Therefore, nutrients have to be supplied for the living cells to exist alive. These cells obtain the nutrients from the capillary vessels existing in the dermis 6. Also, it is known that a concentration of a glucose in the epidermis 4, as mentioned above, changes in direct proportion to the changes in a blood-sugar level.

Additionally, since the constructs such as sweat glands, hair roots, arrector pili muscles do not exist and since there is no blood circulation in the epidermis 4, there exists no factor that changes a scattering state of a light according to heartbeat of the cells (red blood cells, for example) in blood. From the reasons above, measuring a part of the epidermis 4 in the measuring region has quite significant advantages.

On the other hand, plenty of blood flows in the dermis 6 seem to affect the measuring results. However, since the flow of blood stays when the measuring region is hold and stood still at the time of measuring, a glucose concentration is measured without adversely affecting a responsiveness.

In the information detector 12, a depth of a penetrating light 12b into the horny layer 4b can be controlled to a certain degree, by adjusting a size (depth) and an angle of the V-shaped part in the sensing surface 12a. As a particular embodiment of the V-shaped part, it is further preferable that a plurality of grooves are successively provided in parallel, for the reason that a signal can be obtained from each of the plurality of grooves, increasing a total amount of the signals to be obtained.

Additionally, since inner part of the epidermis 4 and/or the dermis 6 is measured by sandwiching the epidermis 4 with the V-shaped part, the horny layer 4 which includes few components that give the necessary information is preferred to be thinner.

Figure 3:
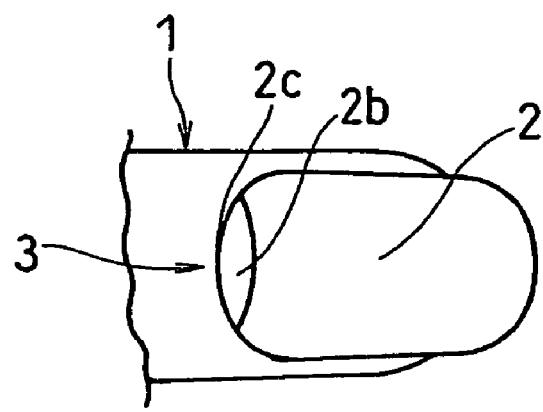
FIG. 3 is a figure illustrating a structure of a finger as a living body.
Figure 3:
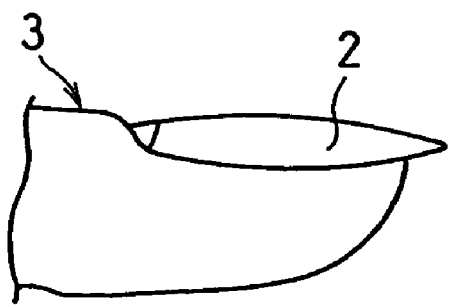
Figure 3:
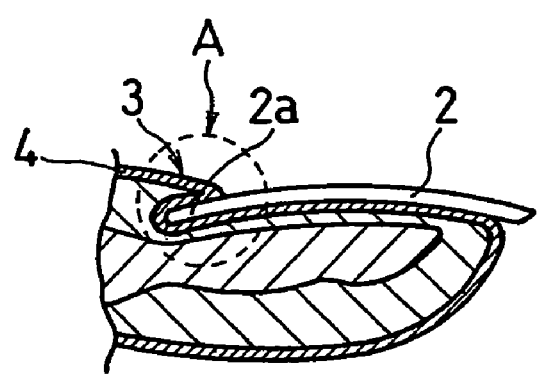
Figure 4:
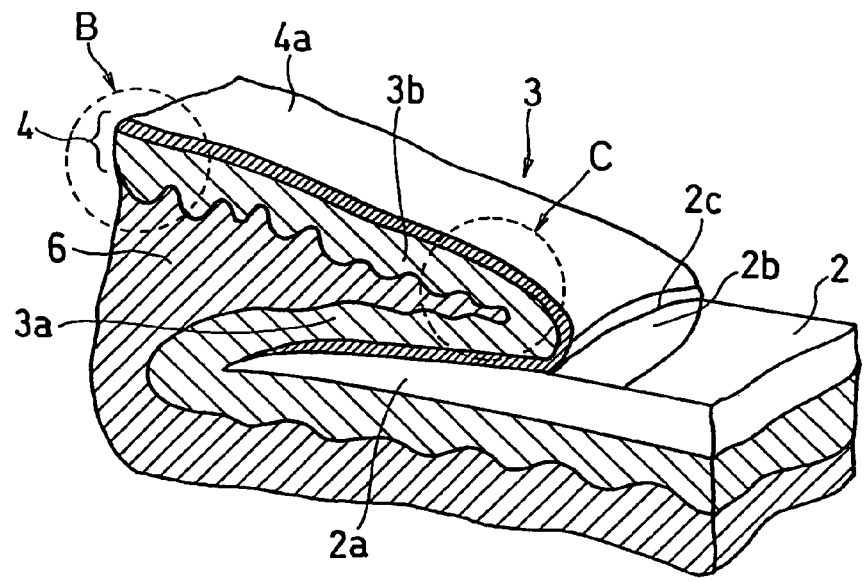
FIG. 4 is a view further illustrating a structure of a finger as a living body in detail.

Next, a preferable part of the finger for the measuring region in the present invention is described with reference to FIGS. 3-6. FIG. 3(a) is a top view of the finger 1, and FIG. 3(b) is a side view of the finger 1. Further, (c) in FIG. 3 is a schematic sectional view of the finger 1. FIG. 4 is an enlarged perspective view of "A" shown in (c) of FIG. 3. Furthermore, FIGS. 5 and 6 are the enlarged perspective view of "B" and "C" in FIG. 4 respectively.

A tip of the finger 1 will be briefly explained in the following. A nail plate 2 which exists in the tip of the finger 1 has its root protected, in the inside of the skin. The nail plate 2 is inserted into the skin obliquely, and a part covering a nail matrix (or nail root) 2a is called a proximal nail fold 3. The nail matrix 2a refers approximately to an area from the edge of a lunura 2b, a semilunar white zone, to a part where the nail is inserted.

Due to the inserted nail plate 2, the epidermis 4 is folded in this part, and a part closely contacting the nail matrix 2a is called a ventral layer 3a and a part on the side of a surface of the finger 1 is called a dorsal layer 3b. These parts are collectively called the proximal nail fold 3. A translucent horny part extending from this proximal nail fold 3 to the nail plate 2 is called an eponychium 2c.

Figure 5:
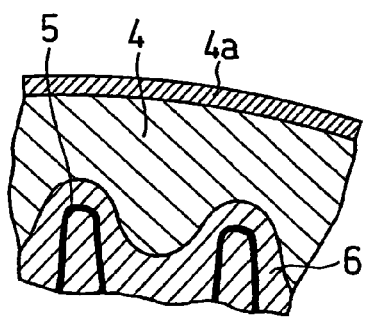
FIG. 5 is a schematic sectional view enlarging a part shown by B in FIG. 4.
Figure 6:
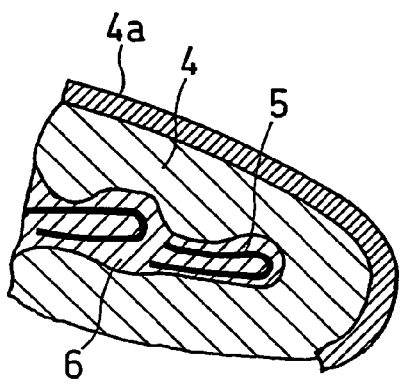
FIG. 6 is a schematic sectional view enlarging a part shown by C in FIG. 4.

As shown in FIG. 5, in the dermis 6, capillary loops 5 in which an artery and a vein are anastomosed exist, and the loop-like shaped parts run in parallel with the part having peaks called a papillary layer in the dermis 6. That is to say, the capillary loops cross at right angles with the horny layer 4a, the outermost layer.

In the dermis 6 in the proximal nail hold 3, as shown in FIG. 6, the capillary loops 5 in which the artery and the vein are anastomosed exist, and the loop-like shaped parts run in almost in parallel with the outermost horny layer 4a, and have a thick diameter.

From the above, as shown in FIG. 5, the epidermis 4 receives nutrients from the upper parts of the capillary loops 5, and as shown in FIG. 6, since the capillary loops 5 run almost in parallel with the outermost horny layer 4a, the epidermis 4 near the proximal nail fold 3 receives nutrients from the entire blood vessel, thereby making the concentration of the components higher than in the other parts. Therefore, as the measuring region, a part around the proximal nail fold 3 among a region from the eponychium 2c to the distal interphalangeal joint 1a is further preferably used.

The structures shown in FIGS. 3 and 4 are described in Comprehensive Handbook of Clinical Dermatology 3A: Structure and Function of Skin I, Nakayama Shoten, 1982, for example.

In a method of the present invention, a measuring region determining means is used for detecting the proximal nail fold 3 as the measuring region. This measuring region determining means can distinguish the skin composed of a soft keratin such as the proximal nail fold 3 from the nail plate 2 composed of a hard keratin, and a difference between the skin and the nail can be detected by light, for example.

For example, the measuring region determining means can detect the eponychium 2c, a part where the nail plate 2 transforms to the skin by detecting a reflected light by applying a light to the finger 1a and determining a difference in spectra of the nail and the skin. The difference in the spectra may be base on a difference in a sulfur content of the nail and the skin. Also, the measuring region determining means may detect the difference based on a lipid content in the nail and the skin.

Also, a difference in a reflectance detected by applying the light to the finger 1 can be used. That is to say, the embodiments are not to be limited thereto, as long as the difference of the nail and the skin can be determined by using a light.

Further, the proximal nail fold 3 can be detected by using an elevation change which exists due to inherent skin structure of the eponychium 2c and the nail plate 2, or the nail plate 2 and the proximal nail fold 3. The difference of the eponychium 2c and the nail plate 2, or the nail plate 2 and the proximal nail fold 3 can also be determined by a video, by recording an image with a CCD camera.

Furthermore, it is preferable that the measuring region determining means has a visual identification means capable of identifying a certain position. As for the visual identification means, a combination of a transparent window, and a reference line which is provided in the reference window for positioning a measuring region can be used. Based on such means, the measuring region can be determined directly by a visual check.

Thus, in the method of the present invention, a region of the proximal nail fold 3 or a region including the proximal nail fold 3, where the capillary loops 5 run almost in parallel with the epidermis and a concentration of a component is possibly higher, is determined and the light is entered to the epidermis 4 and/or the dermis 6 in the region for the measurement. This enables the measurements of the same region every time, thereby stable measurement results can be obtained.

Figure 7:
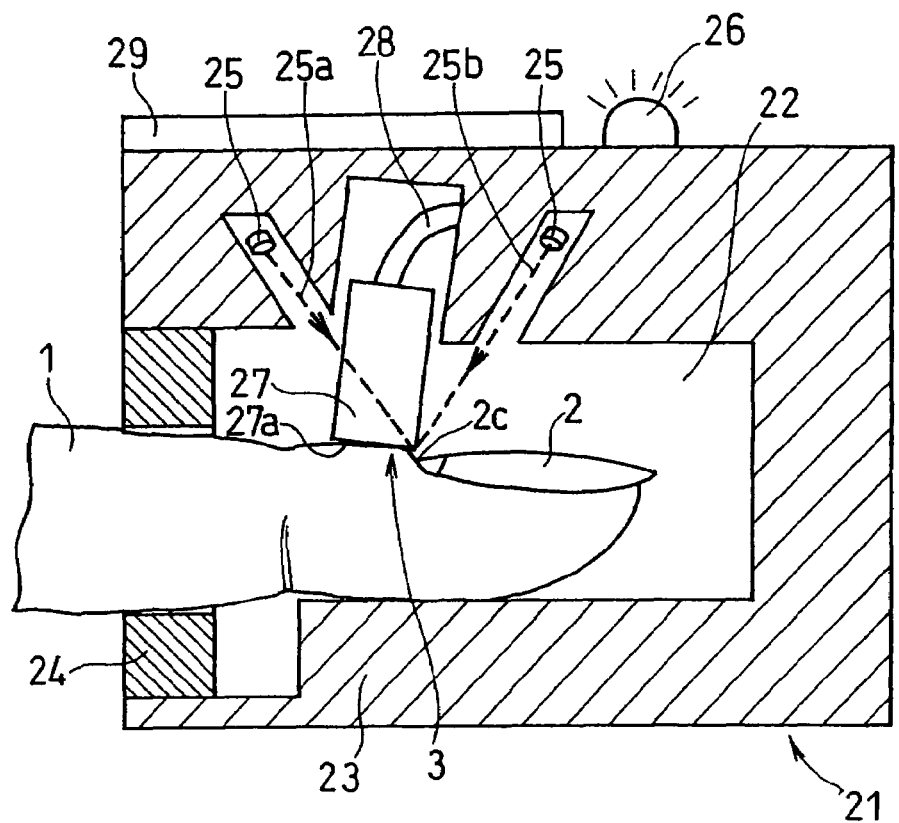
FIG. 7 is a schematic sectional view illustrating a structure of a biological information measuring device according to an embodiment of the present invention.

Next, a measuring device for embodying a measuring method of the present invention is illustrated with reference to FIG. 7. FIG. 7 is a schematic sectional view of the biological information measuring device 21. The biological information measuring device 21 has a hollow 22 to insert the finger 1, a holding table 23 to place the finger 1, and a slot 24. The slot 24 is preferably formed with an elastic body such as a nitrile rubber and provided with an expandable opening. It is further preferable that the slot serves also as a shading means. Also the slot 24 can be in the form of a diaphragm shutter.

Inside the hollow 22, a measuring region determining means 25 is provided. For example, the eponychium 2c, a region where a nail transforms to a skin, is detected by determining the difference of a reflectance of the nail and the skin, after applying a light 25a to the finger 1 inserted from the slot 24, and detecting a reflected light 25b.

Also, it is preferable that a lamp 26 is provided above the biological information measuring device 21, and lit when the eponychium 2c, a region where a nail transforms to a skin, is detected. This can inform a user when the measuring region is inserted.

A measuring means 27 includes an information detector a moving means 28 which is an abutting means so that the information detector can be moved within the hollow 22, and a distal surface 27a of measuring means 27. This moving means 28 is formed to closely contact and press the information detector of the measuring means 27 to the proximal nail fold 3. For example, the moving means 28 is formed to slide upwardly and downwardly. The existing technology such as a gear mechanism can be used, for example.

Also, it is further preferable that a moving distance of the measuring means 27 can be measured by the measuring region determining means.

The distal surface 27a which is formed in the information detector has, as described in the description for FIG. 2, the V-shaped structure in order to pass the light to the epidermis 4 including the horny layer 4a. This distal surface 27a is not limited to the V-shaped structure, as long as the light passes through only to the epidermis 4, like an optical fiber.

Also, the biological information measuring device 21 has, though not shown, the light source, the light detector, and the signal processor, as described in the description for FIG. 1.

This light source can be mounted in the measuring means 27, and can introduce the light to the information detector directly. Also, the light source can be mounted within the biological information measuring device 21 side, to introduce the light to the information detector by using a light guide path, such as an optical fiber.

Here, as a light source, any light source can be used as long as it emits a light having a wavelength, which is absorbed by a subject component to be measured. For example, a Globar light source in which a SiC is sintered into a rod-like shape, a $CO_2$ laser, a tungsten lamp, LD, LED, a halogen light source, and the like may be used.

As a material for the information detector, known materials in the art may be used. For example, a silicon, a germanium, SiC, a diamond, ZnSe, ZnS, or KrS may be used.

Also, as for the light detector, it may be mounted in the measuring means 27 to directly guide the light which exits from the information detector, or it may be mounted in the biological information measuring device 21 side to guide the light using the light guide path such as an optical fiber.

Here, as for the light detector, a known light detector in the art may be used. For example, a pyroelectric sensor or an MCT detector (HgCdTe detector, which is a kind of a quantum type detector) may be used.

The processor is mounted in the biological information measuring device 21 or in the measuring means 27, to process and calculate the information obtained in the light detector, and display a blood-sugar level and the like obtained from the information to a display part 29 provided on the upper side of the biological information measuring device 21.

The biological information measuring device 21 may be provided with a spectroscope, and the processor may be provided with a converting means having a memory part memorizing a standard data showing a relationship of an intensity of a light having a specific wavelength and the concentration of a specific component. For example, the converting means can convert an intensity of an exit light at a specific wavelength detected in the light detector to a concentration of a specific component.

When the finger 1 is inserted from the slot 24 of the biological information measuring device 21, the measuring region determining means 25 detects the eponychium 2c, a region where the nail transforms into the skin, and the lamp 26 provided on the upper side of the biological information measuring device 21 is turned on.

After the inserting of the finger 1 is stopped when the lamp 26 is turned on, the measuring means 27 is moved and descended to closely contact and press the information detector to the proximal nail fold 3, and the measurement is started.

For the starting of the operation of the measuring region determining means 25, a switch may be provided, or, a contact switch may be included in the slot 24, to automatically operate when the finger 1 is inserted. When the eponychium 2c is detected by the measuring region determining means 25, the detection may be recognized by the turning on of the lamp 26, or a sound like a buzzer. Also, a blinking of the display part 29, or a visual display such as a letter illustration, may be used instead of turning on the lamp 26.

Also, to start the movement of the measuring means 27, a switch may be provided. Or, the measuring means may be made to automatically start moving when the measuring region determining means 25 detects the eponychium 2c and further detects the stop of the finger 1. Further, in order to prevent the finger 1 to be out of the position when inserting the finger, the measuring region determining means 25 may be provided at not less than 2 positions (i.e. a plurality of the measuring region determining means 25) with a certain distance in between.

Thus, by detecting and displaying the difference of the nail and the skin, the inserting of the finger can be stopped at the most appropriate position, and the setting of the finger at the same position can be repeated every time.

Figure 8:
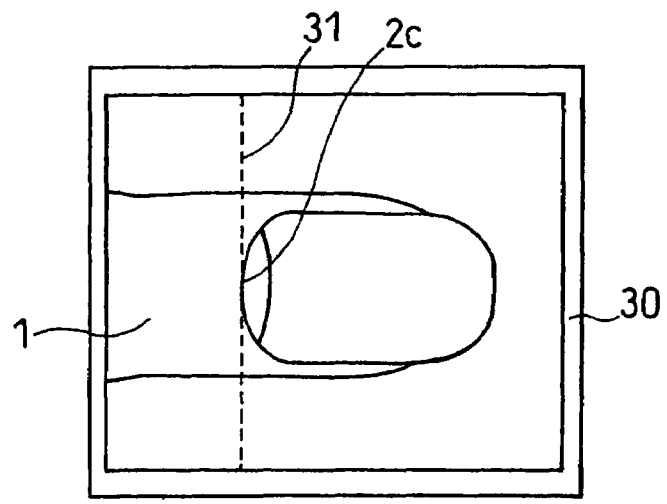
FIG. 8 is a top view for explaining a display part of the present invention.

FIG. 8 is a schematic view illustrating an example of the display part 30 which may be included in the biological information measuring device 21. When a CCD camera is provided in the biological information measuring device 21, though not shown, inside the hollow 22 can be monitored and an obtained image can be displayed on the display part 30.

The reference line 31 is marked at the display part 30, and the position can be determined visually by matching the boundary line between the eponychium 2c and the proximal nail fold 3 with the reference line 31.

Figure 9:
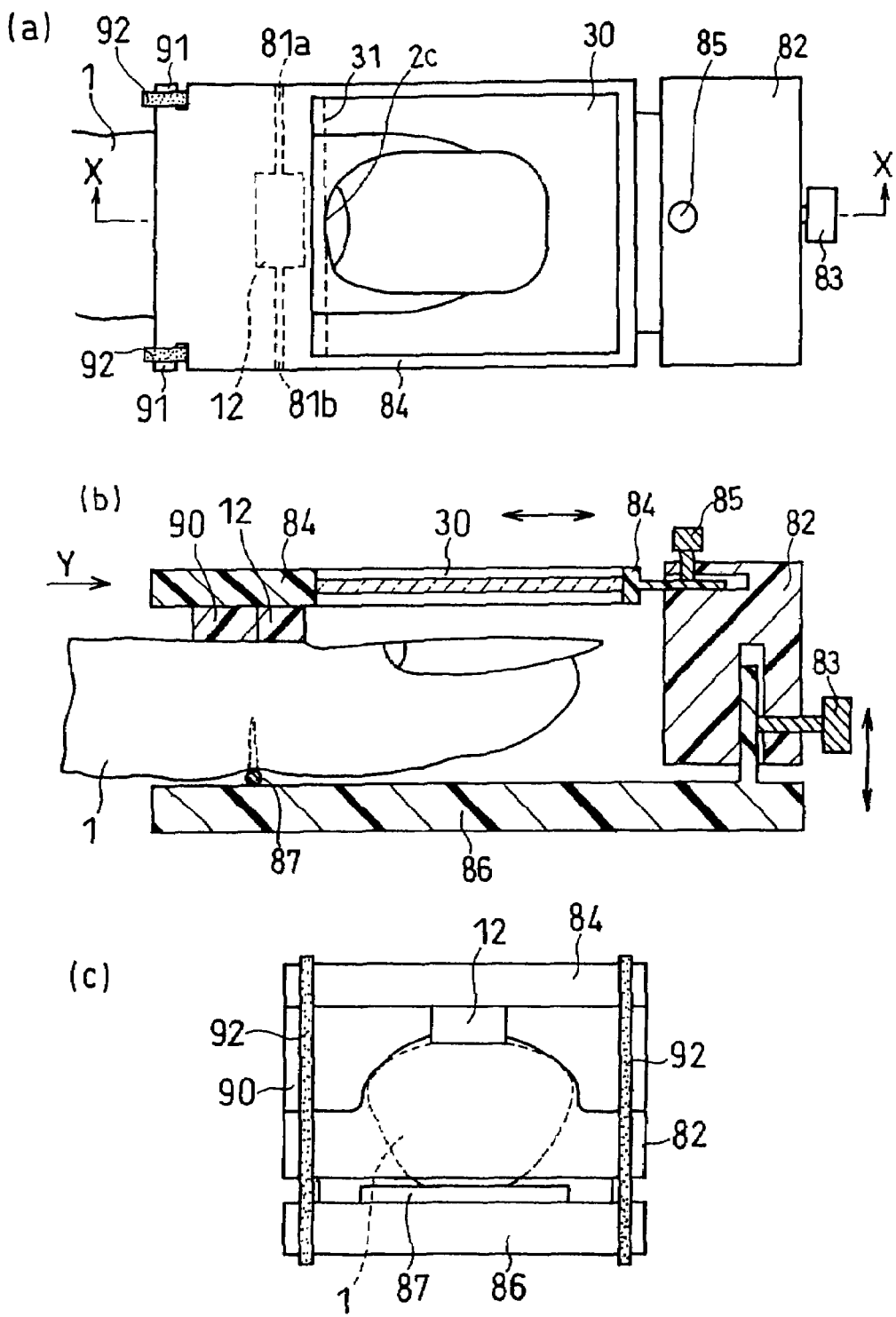
FIG. 9 is a view illustrating a structure of a device for measuring biological information in another embodiment of the present invention.

FIG. 9(a) is a schematic top view illustrating a structure of a biological information measuring device in another embodiment of the present invention. FIG. 9(b) is a sectional view taken on the line X-X in FIG. 9(a). Additionally, FIG. 9 (c) is a front view of the biological information measuring device seen from a direction of an arrow "Y" in FIG.9(b).

According to this biological information measuring device, the inserting of the finger 1 can be directly checked visually, and the information detector 12 can be positioned at a predetermined position of the finger 1.

The information detector 12 and the display part 30 made of a transparent body are fixed on the information detector holding table 84. The display part 30 is marked with the reference line 31, and includes a light entering element 81a for entering the light to the information detector 12, and a light emitting element 81b for guiding the emitted light from the information detector 12 to a spectroscopic element (not shown) and to a light detector (not shown).

The information detector holding table 84 is movable towards the direction of the line X-X, and towards the direction vertical to the line X-X shown in FIG. 9(a), and can be fixed at a desired position by using a screw part 85.

The information detector holding table 84 is attached to the holding table 82, and the holding table 86 is attached to the holding table 82. The height of the information detector holding table 84 can be adjusted and fixed by using the screw part 83, in order for the information detector 12 to appropriately contact the finger 1.

Also, as shown in FIG. 9(c), in the information detector holding table 84, a finger abutting part 90 formed of an elastic body such as a spring and a rubber, a cushion, or a foamed body can be placed beside the information detector 12. Also, in addition to providing a projection 91 on the information detector holding table 84, similar projection (not shown) may be provided in the holding table 86, and the information detector holding table 84 and the holding table 86 can be fixed with a rubber band 92. Thus, a pressure onto the finger 1 will become preferably stable.

On the upper side of the holding table 86, a positioning member 87 can be provided for positioning the finger 1. The positioning member 87 may be formed of a projection or a rib. Thus, the finger 1 can be positioned on the holding table 86 in a stable manner.

Here, an adjusting method for the position of the information detector holding table 84 will be described in detail. First, the finger 1 is inserted in between the display part 30 and the holding table 86. The distal interphalangeal joint 1a of the finger 1 is made to have contact with the positioning member 87, and the finger 1 is hold still at the position making the contact.

Next, the information detector holding table 84 is slid. The part of the eponychium 2c is matched with the reference line 31 of the display part 30 visually, and the information detector holding table 84 is fixed by using the screw part 85.

As to the height of the information detector holding table 84, the position of the information detector holding table 84 may be adjusted to appropriately bring the information detector 12 into contact with the finger 1 by sliding the holding table 82, and then fixed. Thus, the proximal nail fold of the finger 1 can be brought into contact with the information detector 12.

As described above, the measuring region can be easily and reliably brought into contact with the information detector 12 with high repeatability.

Figure 10:
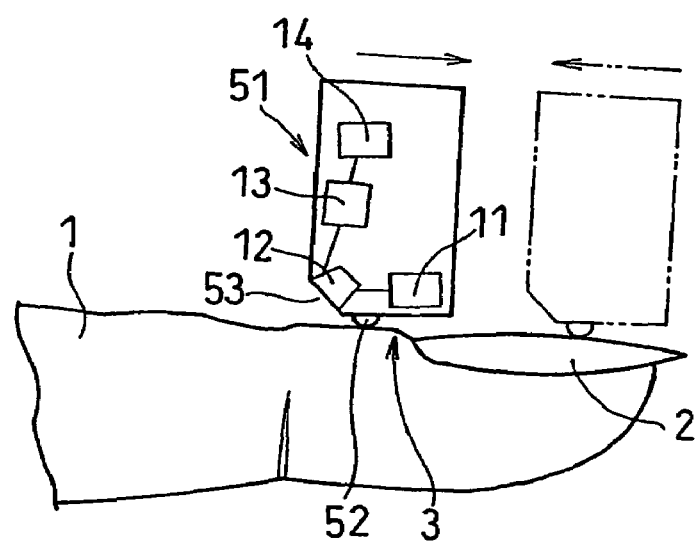
FIG. 10 is view illustrating a structure of a device for measuring biological information in still another embodiment of the present invention.
Figure 10:
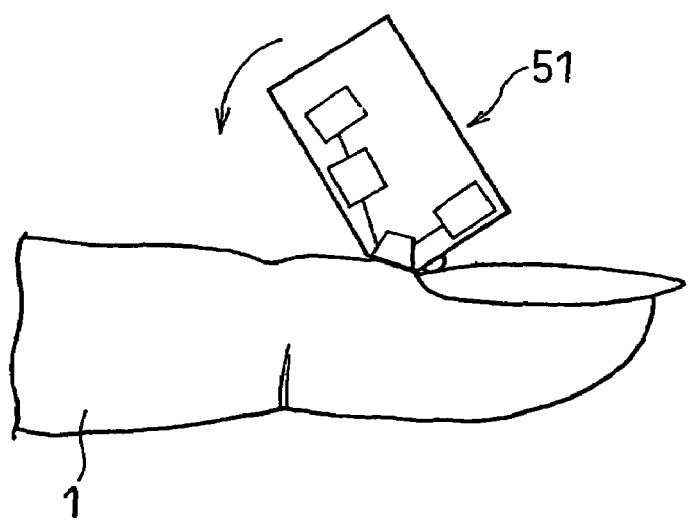

FIG. 10 is a schematic view of the biological information measuring device 51 in still another embodiment of the present invention. In FIG. 10, the same components in FIGS. 1-7 are indicated by the same reference numerals and explanations for these components are omitted.

The biological information measuring device 51 in this embodiment includes a rotatable roller 52 at the bottom surface, and a part of a side surface thereof has a taper 53, the surface of which forming an angle of not less than 90° C. with the bottom side surface. The information detector 12 is mounted in the taper 53, and further, the light source 11, the detector 13, and the signal processor 14 are mounted in as well.

This biological information measuring device 51 also serves as the detector for the proximal nail fold 3. The biological information measuring device 51 is moved towards the nail side from the distal interphalangeal joint 1a of the finger 1, as shown in FIG. 10(a). In this step, when the roller 52 is moved towards the eponychium 2c and the nail plate 2 from the proximal nail fold side, the whole biological information measuring device 51 lowers downward, recognizing that the roller 52 is moved to the position where the elevation changes according to the difference between the nail and the skin. That is to say, it can be determined that the biological information measuring device 51 is moved towards the nail side.

Then, as shown in FIG. 10(b), the biological information measuring device 51 is inclined towards the proximal nail fold 3, to bring the biological information detector 12 into close contact with the proximal nail fold 3.

The measurement can be conducted in such a state. The movement of the biological information measuring device 51 may be conducted manually by hand, or can be conducted automatically by running the device onto the finger 1 to detect the elevation change and to incline.

Also, it is further preferable that the biological information detector 12 is provided with a contact switch, and provided with a structure in which the measurement is started by detecting the contact and the switch is turned on.

The biological information measuring device 51 can also be moved from the nail side as shown in a dotted line, not from the distal interphalangeal joint 1a towards the nail side.

In such a case, the roller 52 is on the nail plate 2 side, and when the taper 53 of the biological information measuring device 51, i.e. information detector 12, is abutted to the proximal nail fold 3, it can determine the position of the proximal nail fold 3. Therefore, for the measurement, the information detector 12 is inclined to the proximal nail fold 3 side, to bring it into the contact.

Thus, in the present invention, the proximal nail fold 3 or the region including the proximal nail fold 3, where the capillary loops 5 run approximately in parallel with the epidermis and a concentration of a content is regarded as higher, is detected, and the measurement is conducted by applying the light only to the inside of the epidermis 4. By detecting the measuring region, the measurement at the same position can be conducted every time, and a stable measurement results can be obtained.

As described above, according to the method and device for measuring biological information of the present invention, since the measuring region can be precisely determined between the eponychium and the distal interphalangeal joint, a concentration of a specific component, i.e. the biological information, can be measured without variations or inconsistency at a stable measuring region appropriate for the measurement of the biological information. Such method and device for measuring biological information of the present invention are useful for the measurement of a blood component, specifically in medical field.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

The invention claimed is:

1. A biological information measuring device for measuring a concentration of a specific component included in a living body, comprising:
   a measuring region determining means for determining a measuring region in between an eponychium and a distal interphalangeal joint, said measuring region determining means determines the measuring region at the proximal nail fold,
   an information detector for applying a light to said measuring region and detecting a light which exits from said measuring region, said information detector includes a portion for contacting the measuring region,
   a light source for entering a light to said information detector contacting said measuring region, said light is applied to the measuring region through said portion for contacting the measuring region,
   a light detector for detecting a light which exits from said information detector contacting said measuring region, said light enters the information detector through said portion for contacting the measuring region, and
   a processor for measuring said specific component based on information obtained from said light detector.

2. The biological information measuring device in accordance with claim 1, comprising an abutting means for abutting said information detector to said measuring region.

3. The biological information measuring device in accordance with claim 1, wherein said measuring region determining means determines said measuring region based on a difference between signal information of light applied to a nail and signal information of light applied to a skin.

4. The biological information measuring device in accordance with claim 1, wherein said measuring region determining means has a visual identification means capable of identifying a certain position.

5. The biological information measuring device in accordance with claim 1, wherein said measuring region determining means determines said measuring region by detecting an elevation change which exists due to skin structure.

6. A biological information measuring method for measuring a concentration of a specific component included in a living body, comprising the steps of:
   (1) determining a measuring region in between an eponychium and a distal interphalangeal joint; said measuring region is at the proximal nail fold;
   (2) detecting a light which exits from said measuring region, after an entrance into said measuring region, with an information detector; said information detector includes a portion for contacting the measuring region; said light is applied to the measuring region through a portion for contacting the measuring region; and said light enters the information detector through said portion for contacting the measuring region; and
   (3) specifying a concentration of a specific component of said measuring region based on the light detected in said step (2).

7. The biological information measuring method in accordance with claim 6, wherein said measuring region is determined based on a difference between signal information of light applied to a nail and signal information of light applied to a skin in said step (1).

8. The biological information measuring method in accordance with claim 6, wherein said measuring region is determined visually in said step (1).

9. The biological information measuring method in accordance with claim 6, wherein said measuring region is determined by detecting an elevation change which exists due to skin structure in said step (1).

* * * * *